(12) United States Patent
Sato et al.

(10) Patent No.: US 6,892,565 B2
(45) Date of Patent: May 17, 2005

(54) GAS SENSOR AND GAS CONCENTRATION DETECTING DEVICE

(75) Inventors: Yoshikuni Sato, Aichi (JP); Hideki Ishikawa, Aichi (JP); Morio Onoda, Aichi (JP); Takeshi Morita, Aichi (JP); Noboru Ishida, Gifu (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 10/379,202

(22) Filed: Mar. 6, 2003

(65) Prior Publication Data
US 2003/0217584 A1 Nov. 27, 2003

(30) Foreign Application Priority Data
Mar. 6, 2002 (JP) .......................... 2002-060651

(51) Int. Cl.⁷ .............................. G01N 29/02
(52) U.S. Cl. ..................... 73/24.01; 73/23.31
(58) Field of Search ............... 73/31.05, 23.32, 73/24.01, 597, 23.31, 24.04, 24.06, DIG. 4, 35.09, 35.11, 861.27, 861.28, 866.5

(56) References Cited

U.S. PATENT DOCUMENTS

| | | | | |
|---|---|---|---|---|
| 4,461,177 A | * | 7/1984 | Feng | 73/587 |
| 4,622,855 A | * | 11/1986 | Sinha et al. | 73/703 |
| 5,351,522 A | * | 10/1994 | Lura | 73/24.01 |
| 5,625,140 A | * | 4/1997 | Cadet et al. | 73/24.01 |
| 6,189,379 B1 | * | 2/2001 | Igarashi et al. | 73/202 |
| 6,279,378 B1 | * | 8/2001 | Sheen et al. | 73/24.01 |
| 6,308,572 B1 | * | 10/2001 | Ishikawa et al. | 73/597 |
| 6,418,782 B1 | * | 7/2002 | Sato et al. | 73/24.01 |

OTHER PUBLICATIONS

M. Habaguchi et al., "Gasoline Vapor Concentration Sensor—On Board Measurement by Ultrasonic Pulse–", Proceedings for Society of Automotive Engineers of Japan 955, 1995–9, pp. 89–92.

* cited by examiner

*Primary Examiner*—Hezron Williams
*Assistant Examiner*—John Fitzgerald
(74) *Attorney, Agent, or Firm*—Sughrue Mion, PLLC

(57) ABSTRACT

A gas sensor includes an element case 42 with an internal peripheral surface formed as a taper surface 100. A portion of a housing section 43 surrounded by the taper surface 100 and a protective film 48 is filled with a filler 49. When the filler 49 thermally expands at high temperature, the filler 49 is subjected to a component of force in an upward direction by the taper surface 100. Therefore, projection of an element portion 44 involving deformation of the protective film 48 is suppressed, a change ΔL of a propagation distance L to a reflecting section 33 is also suppressed, and a detection accuracy never decreases. In addition, reverberation is reduced.

13 Claims, 15 Drawing Sheets

B-B Arrow View

High Temperature State

High Temperature State

Fig. 11

| Taper Angle (°) | Average of Projection Amounts ΔL (mm) |
|---|---|
| 0 | 0.16 |
| 11 | 0.00 |
| 15 | −0.01 |

| Taper Angle (°) | 85°C Reverberation R (μ sec) |
|---|---|
| 0 | 209 |
| 11 | 173 |
| 15 | 247 |

GAS SENSOR AND GAS CONCENTRATION DETECTING DEVICE

The application is based on Japanese Patent Application No. 2002-60651 filed Mar. 6, 2002, the disclosure of which is incorporated herein by reference in its entirety.

BACKGROUND OF THE INVENTION

1. Field of the Invention

The present invention relates in general to a structure of a gas sensor, and more specifically relates to a gas sensor for detecting characteristics of a gas existing in a predetermined flow path.

2. Description of Related Art

Conventionally, a gas sensor measures characteristics (for example, a concentration, a temperature, or a humidity) of a gas existing in a flow path using a detection element. In such a gas sensor, a signal from the detection element is electrically processed and outputted as an electric signal corresponding to the characteristics of the gas. In one example, an ultrasonic type gas sensor, which is provided in transportation equipment with an internal combustion engine (such as an automobile) detects a concentration of gasoline, gas oil, or the like utilizing a change in a propagation speed of an ultrasonic wave. Such a gas sensor is provided, for example, in the middle of a purge line that is connected from a canister mounted on the automobile to an inlet pipe of the internal combustion engine. An evaporated fuel gas containing gasoline or the like passes through a flow path of a predetermined volume formed in the sensor. When a concentration of the gasoline vapor changes, a speed of an ultrasonic wave passing through a medium changes, and this speed change is detected by a receiver of the ultrasonic wave to process a signal and output as a signal corresponding to a gasoline concentration. Usually, the time it takes for the ultrasonic wave outputted from a transmitter to propagate a predetermined distance to reach the receiver is detected to find the gasoline concentration.

Among conventional sensors, there are a few that can directly convert a change in characteristic of a gas into a large electric signal, and an electric signal outputted from the detection element is often feeble. Consequently, an output may change even if a slight force acts on the detection element, and in order to avoid this, a measure is taken such as molding an element main body to be fixed with resin in a conventional detection element. For example, in the above-described ultrasonic type gas sensor, it is a general practice to, after housing an element for transmitting or receiving an ultrasonic wave in a dedicated housing case, filling resin, for example, urethane resin in the housing case to embed and fix the detection element (for example, see JP-A-2000-206099).

However, in such a gas sensor, there is a problem in that a stress is applied to a detection element (such as a vibration element) for detecting an ultrasonic wave due to thermal expansion or the like of molded resin to decrease a detection accuracy, or in some cases, the vibration element is displaced due to the thermal expansion of resin to affect the detection accuracy. For example, in the above-described gas sensor using an ultrasonic wave, in order to isolate an element for transmitting or receiving an ultrasonic wave from a gas which is an object of detection, in some cases, a thin film is provided in an opening portion of a housing case and, after attaching the element on the thin film, the housing case is filled with resin. When such a structure is adopted, a filler inside the housing case of the vibration element thermally expands at the time of high temperature and a stress is generated in the inside thereof. As a result, a phenomenon is observed in which a part of the vibration element projects from the opening portion of the housing case while the thin film is deformed in such a manner as being pushed out by the expanded filler. When the part of the vibration element projects, a propagation distance of an ultrasonic wave also changes, which affects a detection accuracy.

In particular, in the case in which a vibration element (i.e. the detection element) is used for both transmission and reception of an ultrasonic wave, a problem has been pointed out in that an ultrasonic wave reflects around the vibration element (for example, a side or the like of a case of the detection element), whereby noises are generated. An ultrasonic wave which has propagated in a direction other than in a direction along a flow path for detection from the vibration element may reflect on an interface, where a difference of densities of media is large, and then return to the vibration element. This is observed as a noise. If noises are generated in a large quantity and for a long time, it is possible that the noise affects a detection accuracy of an ultrasonic wave.

SUMMARY OF THE INVENTION

The present invention has been devised in order to solve the above-described problems, and it is an object of the present invention to suppress a decrease in a detection accuracy, generation of noises, and the like following a change in temperature in a gas sensor with a structure in which a vibration element (serving as a detection element) in a case is embedded in a filler.

A gas sensor of the present invention for solving at least a part of the above-described problems is a gas sensor for detecting characteristics of a gas existing in a predetermined flow path which includes: a vibration element for detecting the characteristics of the gas utilizing a change in a dilatational wave propagating through the gas; and a tubular element case for housing the vibration element, and is characterized in that an internal peripheral surface of the element case is formed so as to have a smaller inner diameter in a part closer to one end side where the vibration element is arranged, and the vibration element is embedded by a filler filled in the element case.

In such a gas sensor, the vibration element is embedded in the filler filled in the element case. However, since the internal peripheral surface of the element case is formed so as to have a smaller inner diameter in a part closer to one end side where the vibration element is arranged, even if the filler expands, the filler is subjected to a component of force to a side where the inner diameter is large in the internal peripheral surface and deforms to mainly expand to a side where the inner diameter is large. As a result, influence exerted on a change in volume on the side where the inner diameter is small (that is, the side in which the vibration element is provided) becomes small, and even if the filler expands, displacement of a position of the vibration element or a stress applied to the vibration element is suppressed. That is, since the stress generated in the element case due to the expansion of the filler is also reduced on the vibration element side, a phenomenon that a behavior of the vibration element is changed by the stress to decrease an accuracy of detection is also eased.

In order to form the internal peripheral surface of the tubular element case so as to have a smaller inner diameter in a part closer to the one end side where the vibration element is arranged, it is possible to form at least a part of the internal peripheral surface as a taper surface having an inner diameter narrowed toward the one end side or to form at least a part of the internal peripheral surface as a curved surface having a smaller inner diameter in a part closer to the one end side. In the former case, an angle of the taper surface can be set to a range of 7 to 15 degrees with respect to an axial direction. More preferably, the angle may be set to a range of 10 to 12 degrees. In these angle ranges, a displacement of the vibration element in the case in which the filler expands is controlled to be sufficiently small, and noises or the like due to undesired propagation of a dilatational wave are suppressed sufficiently. On the other hand, in the latter case, the curved surface can be made a part of a circle, an ellipse, a parabola, or a hyperbola in a section in an axial direction of the element case. In the case in which the internal peripheral surface is a curved surface, when a propagated dilatational wave reflects on the internal peripheral surface, since directions of reflected waves do not become the same, a peculiar reflected wave or the like is not generated. Note that, in the case in which the internal peripheral surface is formed as a curved surface, it is allowable to form the curved surface as a free curve in the section in an axial direction of the element case. The internal peripheral surface may be formed symmetrically with respect to an axial center of the element case, but it is also allowable to make it asymmetric. If it is made asymmetric, even if the vibration element is placed in the axial center of the element case, reflected waves of a dilatational wave propagated to the perimeter never overlap with each other in the axial center.

The element case can be constituted by a substantially cylindrical housing section and a flange section which is jointly provided at the other end on the opposite side of the one end of the housing section and attaches the element case to the flow path. When such a structure is adopted, attachment of the element case can be made with the flange section, and a position of the vibration element can be moved away from an attachment position of the element case, which is preferable. This is because, if the vibration element and the attachment position of the element case are close to each other, a dilatational wave tends to propagate between the element case and another member to which it is attached, and various noises are easily generated due to unexpected reflection or the like.

In the case in which the housing section and the flange section are separated from each other, it is sufficient to form the taper surface on an internal peripheral surface corresponding to the housing section. A flange may also be formed on the taper surface. Note that the taper surface is not required to be linear but may be a gentle curve if the inner diameter of the element case becomes smaller on the side of the vibration element.

When the internal peripheral surface of the element case is formed as a taper surface, although an external peripheral surface of the housing section may be formed in parallel with an internal peripheral surface thereof, it can be formed unparallel with the internal surface. In this case, if the housing section is formed in a shape in which a thickness of the housing section gradually increases toward one end of the housing section from a joint portion between the housing section and the flange section, a thickness of the element case can be made thinner than one end of the housing section in the joint portion of the housing section and the flange section, and a sufficient strength in the vicinity of one end of the housing section and a deformability of the entire housing section can be realized.

An external peripheral portion of the film partitioning the vibration element and the flow path in which a gas exists can be fixed to an end face at one end of the element case. The film is useful for protecting the inside of the element case from the gas existing in the flow path. However, as described above, in the case in which the thickness of one end of the housing section provided in the element case is formed thick, there is also an advantage that, in particular, fixing of the film becomes easy.

The vibration element is an element for detecting characteristics of a gas utilizing a change in a dilatational wave propagating through the gas. As such a dilatational wave, an acoustic wave or an ultrasonic wave can be used. In this case, as the vibration element, a vibration element for generating and/or receiving the acoustic wave or the ultrasound wave, for example, a piezoelectric element can be adopted.

The gas sensor of the present invention can be mounted on equipment mounted with a heat engine which burns using a volatile fuel and used for a gas concentration detecting device for detecting a concentration of the volatile fuel. In this case, it is sufficient to form a flow path for detection as a flow path provided in a part of a fuel path to the heat engine. In addition, it is sufficient to connect an arithmetic circuit to a vibration element of the gas sensor to calculate a concentration of the fuel in the flow path, by detecting a speed of a dilatational wave (which is generated by vibration of the vibration element) passing through the flow path, with this arithmetic circuit. This gas concentration detecting device can detect a concentration of vapor of a volatile gas existing in the flow path (for example, gasoline or gas oil) according to a change in a propagation speed of a dilatational wave such as an ultrasonic wave.

BRIEF DESCRIPTION OF THE DRAWINGS

FIG. 11 is a table showing results of an experiment in which a projection amount ΔL of an element portion 44 was measured with respect to three types of taper angle;

DESCRIPTION OF REFERENCE NUMERALS

Figure 1:
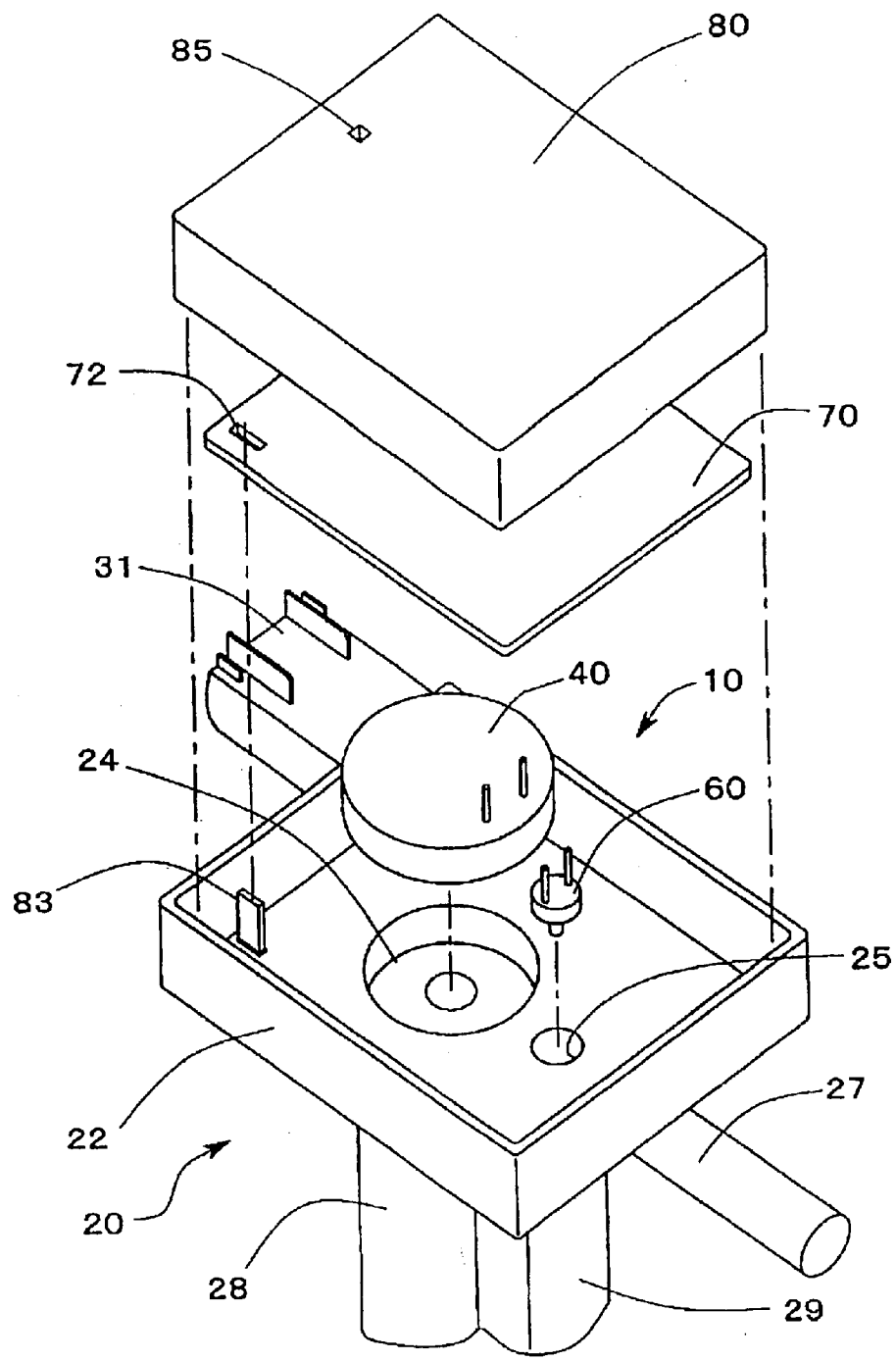
FIG. 1 is an exploded perspective view of a gas sensor 10 according to a first embodiment.

10 . . . Gas sensor
20 . . . Flow path forming member
22 . . . Housing section
22a . . . Projected portion
24 . . . Recessed portion
25 . . . Insertion hole
27 . . . Introducing path
28 . . . Measurement chamber
29 . . . Bypass flow path
31 . . . Connector
31a to 31d . . . Terminals
32 . . . Introducing hole
33 . . . Reflecting section
34 . . . Outlet
35 . . . Discharge flow path
36 . . . Metal plate
37 . . . Recessed portion
38 . . . Opening portion
40 . . . Detection element main body
41 . . . Flange section
42 . . . Element case
43 . . . Housing section
44 . . . Element portion
45 . . . End face
46 . . . Step portion
48 . . . Film
49 . . . Filler
50 . . . Acoustic matching plate
51 . . . Piezoelectric element
52 . . . Tube body
52a . . . Film
52b . . . Adhesion layer
52c . . . Copper foil
53 . . . Openings
54a, 54b . . . Lead wires
55a, 55b . . . Terminals
56a, 56b . . . Projecting portions
59 . . . Projection
60 . . . Thermistor
70 . . . Electronic circuit substrate
72 . . . Attachment hole
80 . . . Case
83 . . . Cut-raised portion
85 . . . Insertion hole
88 . . . Cushion material
91 . . . Microprocessor
92 . . . D/A converter
93 . . . Driver
96 . . . Amplifier
97 . . . Comparator
100 . . . Taper surface
200 . . . Internal peripheral surface
240 . . . Detection element main body
243 . . . Housing section

DETAILED DESCRIPTION OF THE INVENTION

Modes for carrying out the present invention will be hereinafter described based upon an embodiment. FIG. 1 is a disassembled perspective view of a gas sensor as a non-limiting illustrative embodiment of the present invention. This gas sensor 10 is a sensor for detecting a concentration of gasoline vapor utilizing the fact that a propagation speed of an ultrasonic wave changes according to a gas concentration. This gas sensor is arranged, for example, in a passage for purging gasoline from a canister, which is mounted on a vehicle using an internal combustion engine as a power source, to an inlet passage and used for the purpose of detecting a concentration of the gasoline to be purged, and the like.

(A) The Gas Sensor 10

As shown in FIG. 1, the gas sensor 10 includes: a flow path forming member 20 for forming a flow path through which a gas, a concentration of which is to be detected, passes; a detection element main body 40 which is housed in a housing section 22 integrally formed in this flow path forming member 20; a thermistor 60 for detecting a temperature of a gas passing through the flow path; an electronic circuit substrate 70 arranged above the detection element main body 40; and a metal case 80 to be fit in the housing section 22. The detection element main body 40 is fixed to a recessed portion 24 provided in the housing section 22 by ultrasonic welding, and the thermistor 60 is inserted in and fixed to an insertion hole 25. As discussed later, the detection element main body 40 and the thermistor 60 have a terminal for exchanging electric signals, and this terminal is inserted in a corresponding attachment hole of the electronic circuit substrate 70 and fixed by soldering. The gas sensor 10 is manufactured by, after fixing the detection element main body 40 and the thermistor 60 to the housing section 22, attaching the electronic circuit substrate 70 to the housing section 22, further fitting the case 80 in the housing section 22, and then molding all of them with resin, for example, urethane resin.

(B) The Flow Path Forming Member 20

The flow path forming member 20 of the gas sensor 10 is made by forming synthetic resin containing a glass filler. Elasticity thereof is adjusted to a value suitable for a gas sensor. As shown in FIG. 1, the flow path forming member 20 is provided with the housing section 22 for housing the detection element main body 40 above it and has a flow path through which a gas for detection flows below the housing section 22. As a main flow path, an introducing path 27 for introducing a gas containing gasoline vapor into the gas sensor 10, a measurement chamber 28 for detecting a gasoline concentration in this gas with an ultrasonic wave, and a bypass flow path 29 for allowing the gas to bypass the measurement chamber 28 are formed. The measurement chamber 28 and the bypass flow path 29 are provided substantially directly below the detection element main body 40 and substantially directly below the thermistor 60, respectively.

Figure 2:
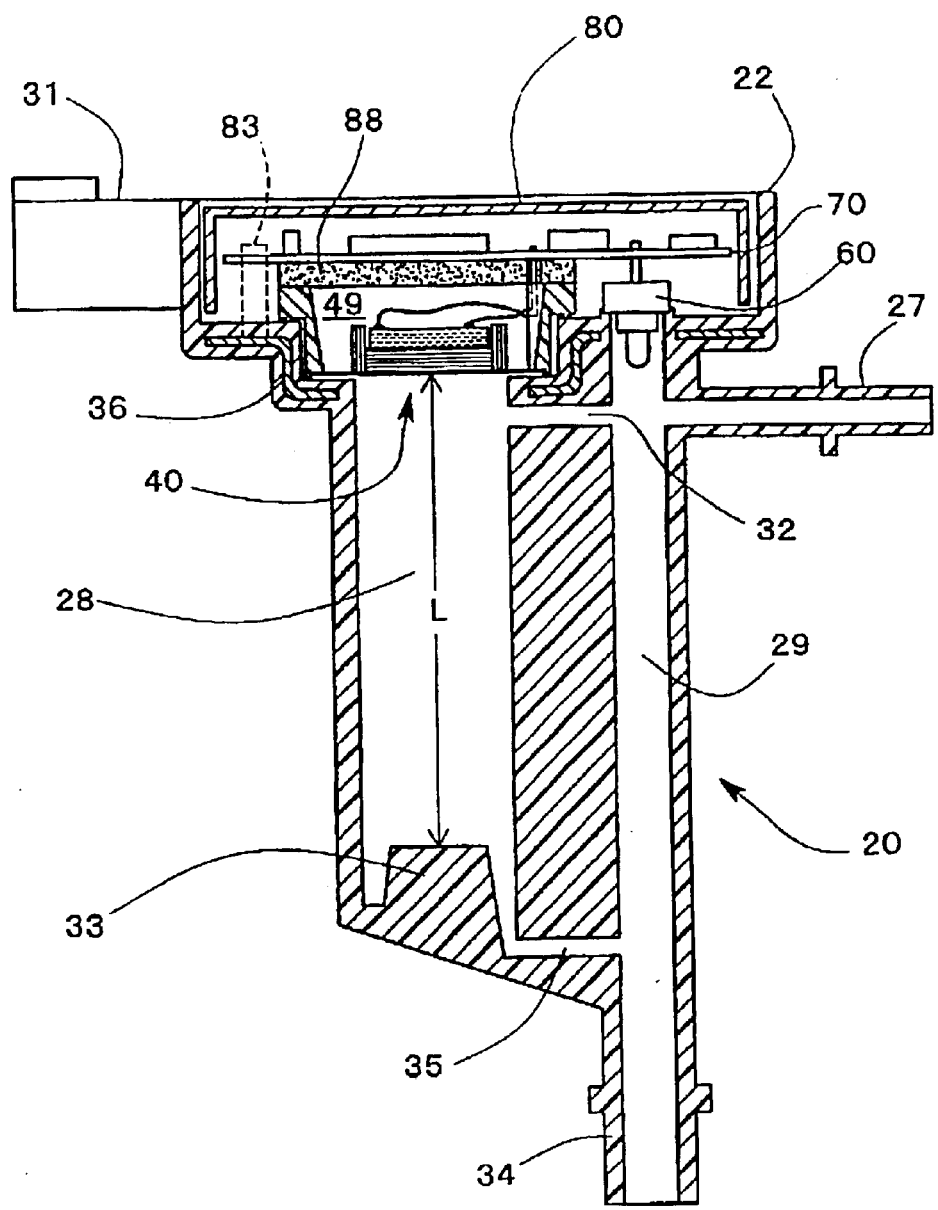
FIG. 2 is a sectional view showing a structure of the gas sensor 10.

A vertical section of the gas sensor 10 is shown in FIG. 2. FIG. 2 is a sectional view of the gas sensor 10 taken along a plane including axial lines of the introducing path 27 and the detection element main body 40. Note that, in FIG. 2, although the gas sensor 10 is finally filled with resin, for example, urethane resin and molded, the resin for molding the entire gas sensor is not illustrated for simplicity of illustration. As shown in FIG. 2, if attention is paid to the flow path, an inside of the flow path forming member 20 is divided into the introducing path 27, the measurement chamber 28, and the bypass flow path 29. The introducing path 27 communicates with the bypass flow path 29 at a right angle and also communicates with the measurement chamber 28 via an introducing hole 32. An outlet 34 is formed in a lower part of the bypass flow path 29. A gas containing gasoline vapor introduced from the introducing path 27 is discharged from the outlet 34. In this embodiment, the outlet 34 is connected to the inlet passage of the internal combustion engine by a not-shown hose. An end on the opposite side of the outlet 34 of the bypass flow path 29 is formed as an insertion hole 25 to which the thermistor 60 is attached. Therefore, the thermistor 60 detects a gas flowing in from the introducing path 27 with a predetermined relation with a temperature of the gas.

An upper part of the measurement chamber 28 communicates with the recessed portion 24 to which the detection element main body 40 is attached, and a reflecting section 33 for reflecting an ultrasonic wave is formed below it. A distance of propagation of an ultrasonic wave from the detection element main body 40 to the reflecting section 33 is referred to as a propagation distance L. Functions of the propagation distance L and the reflecting section 33 will be described later. The reflecting section 33 has a structure in which it is raised by a predetermined distance (several millimeters in this embodiment) from the bottom of the measurement chamber 28. A gap around this reflecting section 33 is directly connected to the bypass flow path 29 via a discharge flow path 35 communicating with the bottom of the measurement chamber 28. Consequently, the gas flowing in from the introducing path 27 through the introducing hole 32 fills inside the measurement chamber 28 and exits to the bypass flow path 29 from the discharge flow path 35 at a predetermined rate. Note that, since the discharge flow path 35 is provided in the bottom of the measurement chamber 28, in the case in which water vapor, gasoline vapor, or the like in the measurement chamber 28 condensed and liquefied, the discharge flow path 35 also functions as a drain for discharging water drips or oil drips. An external shape around the reflecting section 33 is inclined toward the discharge flow path 35 such that liquid accumulated in a groove around the reflecting section 33 is easily discharged.

Figure 3:
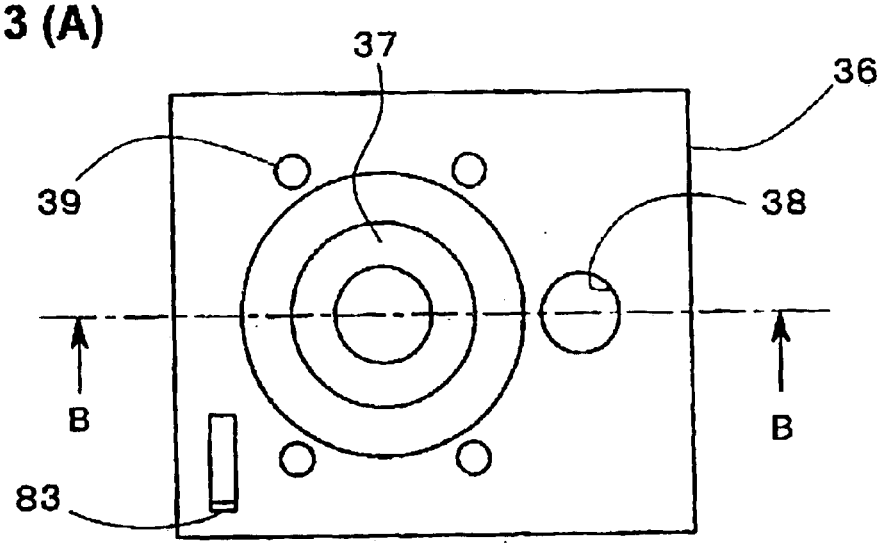
FIGS. 3(A–C) are schematic views of a metal plate 36 insert-molded in a flow path forming member 20.
Figure 3:
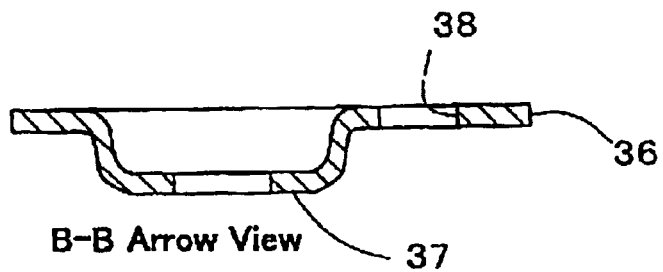
Figure 3:
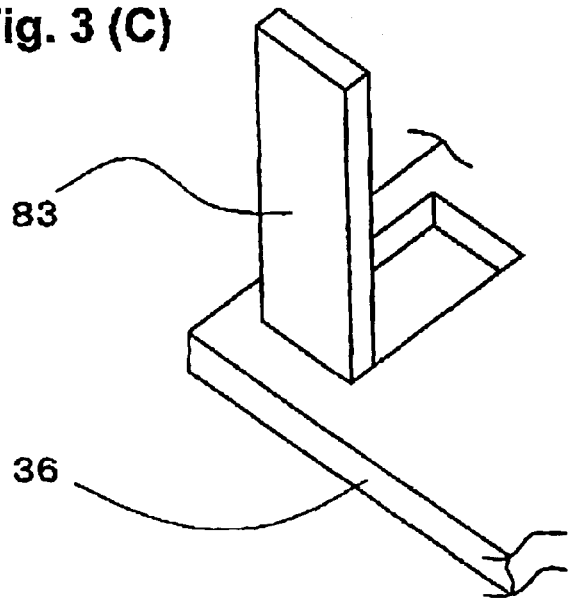

As described above, in the housing section 22 formed in the upper part of the flow path forming member 20, the recessed portion 24 having an opening communicating with the measurement chamber 28, the insertion hole 25 for attaching a thermistor, and the like are formed. A metal plate 36 shown in FIG. 3 is insert-molded in a place equivalent to this housing section 22. As shown in the figure, this metal plate 36 has a shape substantially following a bottom surface shape of the housing section 22 and has a recessed portion 37 corresponding to the recessed portion for attachment 24, an opening portion 38 corresponding to the insertion hole 25. This metal plate 36 includes a cut-raised portion 83 at its one corner. As shown in FIG. 1, after being insert-molded, this cut-raised portion 83 is brought into a state in which it is vertically provided on the inner side of the housing section 22 and, when the electronic circuit substrate 70 is attached, the cut-raised portion 83 is inserted in an attachment hole 72 on the substrate. A land connected to a ground line is prepared in the attachment hole 72, and the cut-raised portion 83 is soldered to this land.

Figure 4:
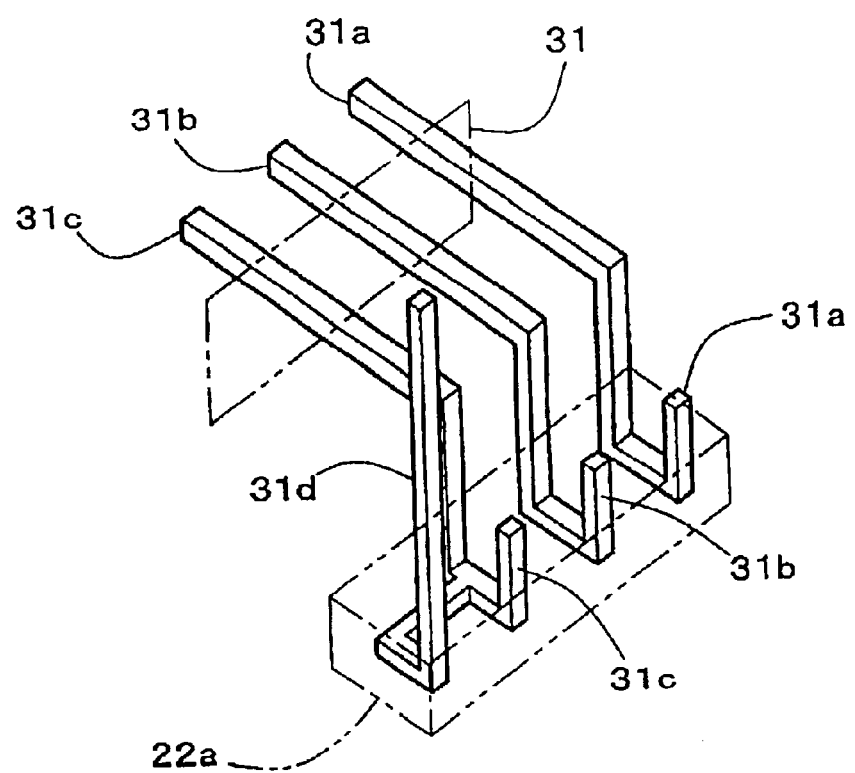
FIG. 4 is a perspective view of terminals 31a to 31d provided in a connector 31.

In one part adjacent to the cut-raised portion 83 among four inside corners of the housing section 22, a projected portion 22a is provided which is also used as a support base for mounting the electronic circuit substrate 70 (see FIG. 4). On the outside thereof, a connector 31 for exchanging an electric signal is formed, and terminals forming the connector 31 penetrate through an external wall of the housing section 22 in this part. Three terminals are prepared for the connector 31 on its entrance side. The two side terminals of the three terminals serve as power supply lines (grand and DC voltage Vcc) for supplying a power to this gas censor 10 from the outside, and the center terminal serves as a signal output line SGNL from the gas sensor 10. The number of the terminals of this connector 31 is four (31a to 31d) as shown in FIG. 4 on the housing section 22 side. This is because the terminal 31c for the ground line has a shape branched into two in the middle. One of the two branched terminals 31d is extended upward and inserted in an insertion hole 85 prepared in a corresponding position of the case 80. After the insertion, the terminal 31d is soldered or brazed to the case 80. As a result, the entire case 80 is electrically coupled to the ground line. In the remaining two parts among the corners of the housing section 22, a not-shown support base is formed for the purpose of mounting the electronic circuit substrate 70.

(C) The Detection Element Main Body 40

Figure 5:
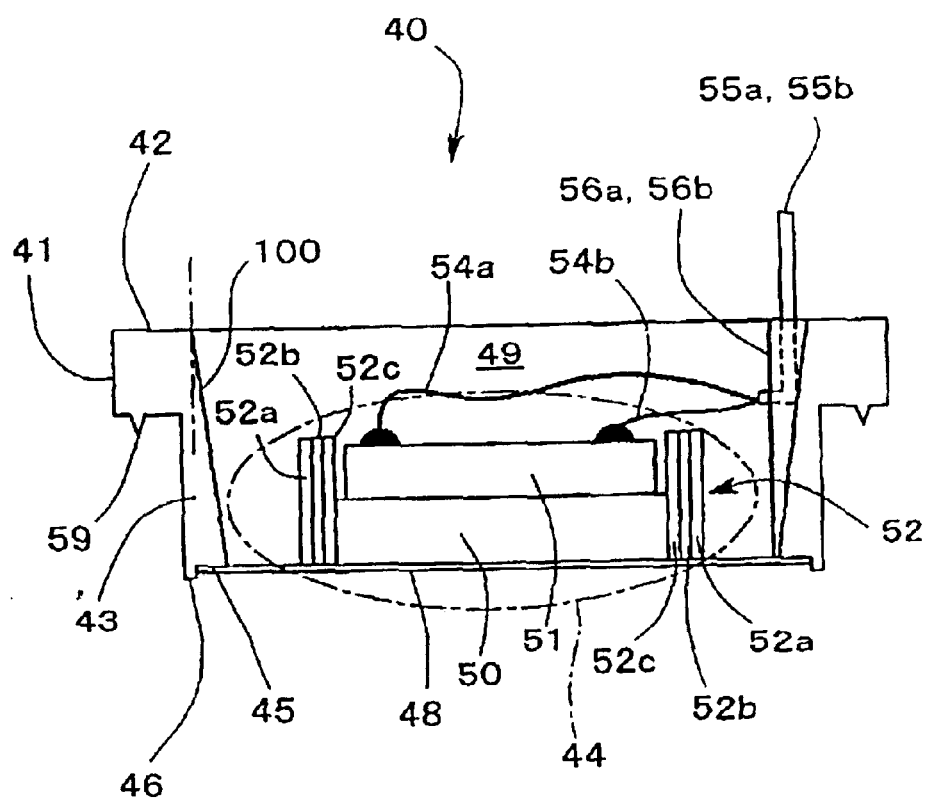
FIG. 5 is a sectional view of a detection element main body 40.

A structure of the detection element main body 40 is shown in a sectional view of FIG. 5. As shown in FIG. 1, the detection element main body 40 is formed in a disk shape after assembly. This is because, after housing a piezoelectric element discussed later and the like inside an element case 42 made of synthetic resin having a flange section 41, resin (for example, urethane resin) is filled inside. The flange section 41 of the element case 42 is formed in a diameter larger than the recessed portion 24 provided in the housing section 22, and the housing section 43 below the flange section 41 is formed in a diameter smaller than the recessed portion 24. In a state in which this element case 42 exists independently, a lower surface of the housing section 43 is opened and a step portion 46 is formed in an outside edge of an end face 45 thereof. At the time of manufacturing, a circular protective film 48, which is fabricated from a material having an anti-gasoline property, is adhered to an inside of this step portion 46.

An acoustic matching plate 50 of a columnar shape is adhered and fixed to a center of the protective film 48, and a piezoelectric element 51 is adhered and fixed to an upper surface of this acoustic matching plate 50. The acoustic matching plate 50 is provided for transmitting vibration of the piezoelectric element 51 into the air (to the measurement chamber 28 in this embodiment) efficiently via the protective film 48. Since an acoustic wave and an ultrasonic wave easily reflect in a place where there is a difference of densities of media, vibration of the piezoelectric element 51 can be transmitted into the measurement chamber 28 as an ultrasonic wave efficiently by jointing the piezoelectric element 51 to the protective film 48 via the acoustic matching plate 50 rather than adhering it directly thereto. In this embodiment, a plate formed by hardening a large number of small glass balls with epoxy resin was used as the acoustic matching plate 50. In addition, a tube body 52 is arranged so as to surround the acoustic matching plate 50 and the piezoelectric element 51. This tube body 52 is formed by sticking a copper foil 52c to a polyethylene terephthalate film 52a via an adhesion layer 52b and is rolled in a tubular shape with the copper foil 52c side being inside to fit and stick end faces together. Since an inner diameter of this tube body 52 substantially matches an external shape of the acoustic matching plate 50, the tube body 52 is in close contact with an external periphery of the acoustic matching plate 50. Both of them are not adhered. As shown in FIG. 5, a portion constituted by the acoustic matching plate 50, the piezoelectric element 51, and the tube body 52 is referred to as an element portion 44.

The piezoelectric element 51 is an electrostrictive element such as piezoelectric formed in a flat columnar shape and is cut out with directions of gratings arranged such that distortion occurs only in an axial direction when a voltage is applied to electrodes formed on its upper and lower surfaces in the axial direction. As described later, the piezoelectric element 51 functions as a transmitter for transmitting an ultrasonic wave into the measurement chamber 28 and, at the same time, in this embodiment, also functions as a receiver for receiving ultrasonic vibration and outputting an electric signal. It is to be appreciated, however, that it is also possible to provide an element for transmission and an element for reception separately to make a gas sensor. As the piezoelectric element 51, a crystal such as piezoelectric ceramics or a rock crystal can be used appropriately. Although not specifically illustrated, the electrodes may be formed with a technique such as vapor deposition on the upper and lower surfaces of the piezoelectric element 51 or may be formed by sticking a metal thin plate to the electrodes.

Figure 6:
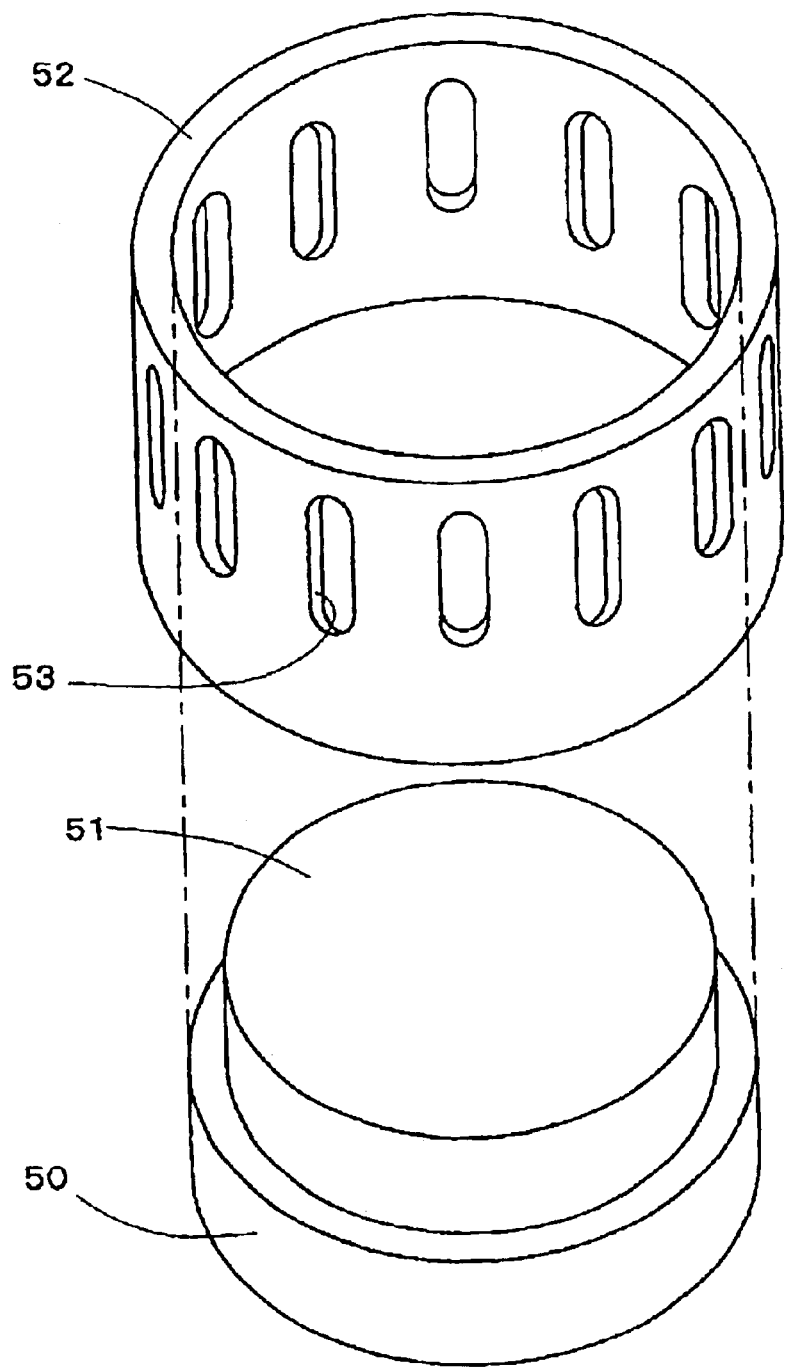
FIG. 6 is an exploded perspective view of an acoustic matching plate 50, a piezoelectric element 51, and a tube body 52.

An outer diameter of this piezoelectric element 51 is made smaller than an outer diameter of the acoustic matching plate 50. Therefore, a gap is formed between an inner surface of the tube body 52 surrounding the piezoelectric element 51 and sides of the piezoelectric element 51. A relationship between the tube body 52 and the acoustic matching plate 50 and piezoelectric element 51 is shown in FIG. 6. FIG. 6 is a disassembled perspective view showing the relationship between the acoustic matching plate 50 and piezoelectric element 51 and the tube body 52. As shown in the figure, twelve openings 53 are provided in the tube body 52. These openings 53 are provided in positions offset upward along the axial direction of the piezoelectric element 51. Therefore, after assembly, the openings 53 of the tube body 52 exist in positions corresponding to the external periphery of the piezoelectric element 51 rather than the external periphery of the acoustic matching plate 50. Note that, in FIG. 6, for convenience of understanding, respective layers 52a, 52b, and 52c forming the tube body 52 are drawn integrally.

As shown in FIG. 5, the element case 42 is formed in a substantially reverse "L" shape on its section, and an internal peripheral surface thereof is formed as a taper surface 100 having a predetermined angle with respect to a vertical surface and is formed to have a smaller inner diameter on a side closer to the end face 45 of the housing section 43. The angle defined by this taper surface 100 with respect to the vertical direction is 11 degrees in this embodiment. Therefore, the external wall of the housing section 43 becomes thicker toward a lower part, that is, the protective film 48. As a result, the housing section 43 of the element case 42 has the external wall which is thin and excellent in flexibility in the vicinity of its joint with the flange section 41, and in its lower end, an area sufficient for sticking the protective film 48 is prepared. Although this element case 42 is formed substantially in a columnar shape, it has projecting portions 56a and 56b in which terminals 55a and 55b are embedded. The terminals 55a and 55b embedded in the projecting portions 56a and 56b are bent in an "L" shape and their upper and lower ends are exposed from the element case 42. Lead wires 54a and 54b are soldered to the lower ends. The upper ends of the terminals 55a and 55b are inserted in corresponding attachment holes of the electronic circuit substrate 70 and soldered to a land prepared in that place. After finishing attachment of the lead wires 54a and 54b of the piezoelectric element 51 in this way, resin such as urethane resin is filled inside the element case 42. This resin is referred to as a filler 49.

The element case 42 includes a projection 59 for welding in a circular shape substantially in a center of the lower surface of the flange section 41. This projection 59 is melted at the time of ultrasonic welding and firmly adheres the flange section 41 to the recessed portion 24 of the housing section 22.

Turning back briefly to FIG. 2, a cushion material 88 may be provided in the flow path forming member 20 in the vicinity of the detection element main body 40. The cushion material 88 is comprised of porous silicone, so as to prevent a reverberation of the piezoelectric element 51, which reverberation tends to occur if another acoustically different filler made of urethane resin is filled in the housing section 22 to contact the inner filler 49. Insertion of such porous material limits air between the fillers, thereby preventing the air to change greatly in volume as a function of temperature as well as preventing a thermal stress affecting the filler 49 and the piezoelectric element 51.

(D) The Electronic Circuit Substrate 70, its Circuit, and a Technique of Gas Concentration Detection Next, a structure of the electronic circuit substrate 70 and attachment thereof will be described. The electronic circuit substrate 70 is a glass epoxy substrate on which a circuit pattern is formed in advance by etching or the like, and lands or through-holes are provided in positions for attaching components. In addition, as already described, in portions to which the detection element main body 40, the thermistor 60, the terminals 31a to 31c of the connector 31, the cut-raised portion 83, or the like are attached, attachment holes of a size according to shapes of the respective terminals are provided, and a land pattern surrounds them. Therefore, in the completed electronic circuit substrate 70, various components for signal processing, for example, an integrated circuit (IC) for signal processing, a resistor, a capacitor, and the like are attached to predetermined positions. This is mounted and soldered on the housing section 22 after the attachment of the detection element main body 40 and the thermistor 60 has been completed, whereby an electric circuit configuration is completed. As manufacturing of the gas sensor 10, resin molding is performed finally.

Figure 7:
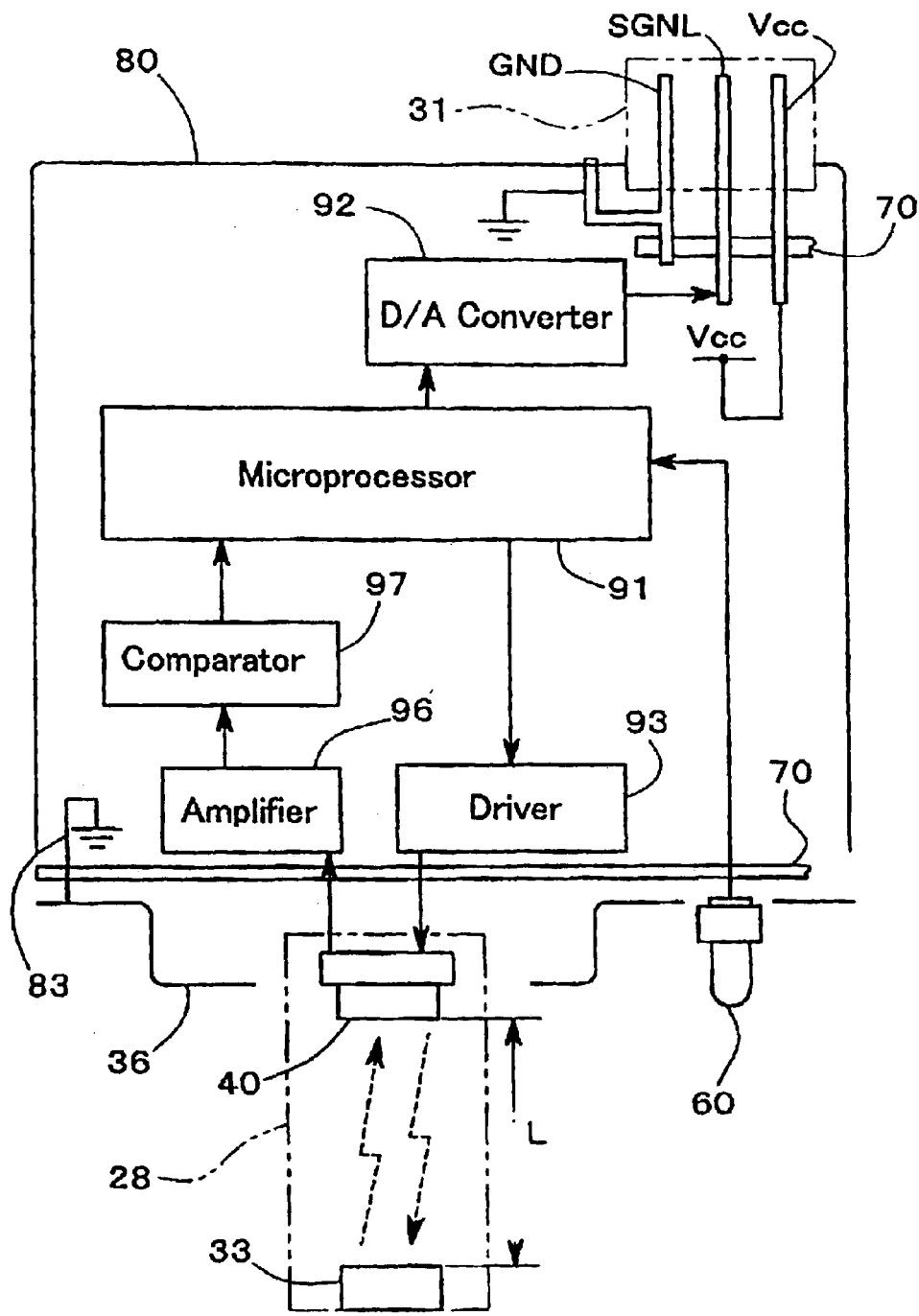
FIG. 7 is a schematic view of an electric structure of an electronic circuit substrate 70.

An electric structure of the gas sensor 10 completed in this way is shown in a block diagram of FIG. 7. As shown in the figure, this electronic circuit substrate 70 includes a microprocessor 91 as a main component and also includes respective circuit elements connected to the microprocessor 91, that is, a digital/analog converter (D/A converter) 92, a driver 93, a comparator 97 to which an amplifier 96 is connected, and the like. The thermistor 60 is directly connected to an analog input port PAP of the microprocessor 91. In addition, the driver 93 and the amplifier 96 are connected to the detection element main body 40.

Upon receiving an instruction from the microprocessor 91, the driver 93 outputs plural rectangular waves. Upon receiving signals of these rectangular waves outputted by the driver 93, the piezoelectric element 51 vibrates and functions as a transmitter to transmit an ultrasonic wave into the measurement chamber 28.

Figure 8:
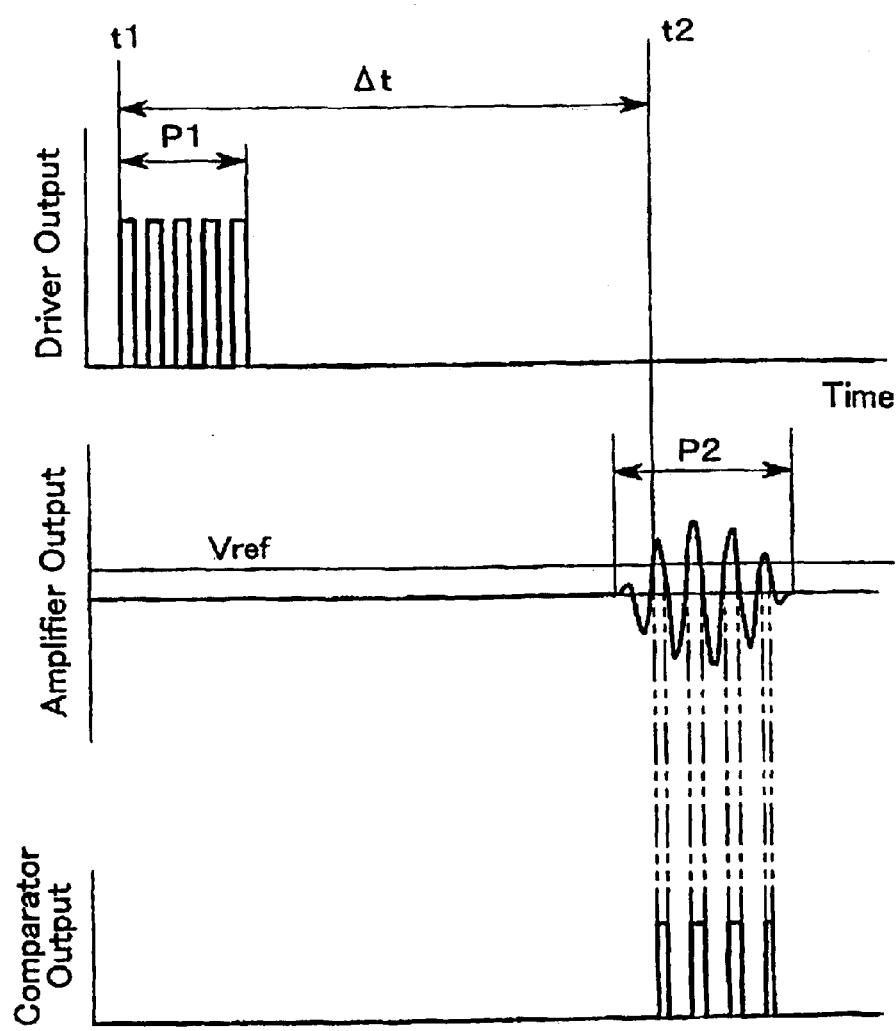
FIG. 8 is a time chart illustrating a principle of detection of a gas concentration using an ultrasonic wave.

The ultrasonic wave transmitted into the measurement chamber 28 travels straight ahead while keeping relatively high directivity and reflects on the reflecting section 33 of the bottom portion of the measurement chamber 28 to return. When the ultrasonic wave which has returned reaches the protective film 48, its vibration is transmitted to the piezoelectric element 51 via the protective film 48 and the acoustic matching plate 50, and the piezoelectric element 51 then functions as a receiver to output an electric signal according to the vibration. This state is shown in FIG. 8. In the figure, a section P1 and a section P2 represent a period during which the piezoelectric element 51 receives the signal from the driver 93 and functions as the transmitter, and a period during which the vibration is transmitted to the piezoelectric element 51 by the ultrasonic wave reflected on the reflecting section 33 and the piezoelectric element 51 functions as the receiver, respectively.

The signal of the piezoelectric element 51 at the time when it functions as the receiver is inputted in the amplifier 96 and amplified. An output of this amplifier 96 is inputted in the comparator 97 and compared here with a threshold value Vref prepared in advance. The threshold value Vref is at a level in which an error signal outputted by the amplifier 96 due to an influence of a noise can be distinguished. As the error signal, in addition to one due to a noise, there is one due to an influence of a reverberation or the like which the detection element main body 40 itself has. Although the piezoelectric element 51 is adhered to the acoustic matching plate 50 and filled with resin such as urethane resin, since it is capable of performing free end vibration to some extent, it may perform damped vibration over a predetermined period even after a drive signal outputted from the driver 93 is lost. In addition, there is also a slight ultrasonic vibration propagating from the piezoelectric element 51 to its periphery, and vibration which is caused by the ultrasonic vibration reflecting on an interface of the element case 42 or the like to return also exists. These become reverberations.

The comparator 97 compares the signal from the amplifier 96 with the threshold value Vref, thereby reversing its output when a magnitude of vibration received by the piezoelectric element 51 becomes equal to or larger than a predetermined magnitude. By monitoring the output of the comparator 97 with the microprocessor 91 and measuring a time Δt from an output timing (timing t1 of FIG. 8) of a first ultrasonic wave from the piezoelectric element 51 until a timing (timing t2 of FIG. 8) when the output of the comparator 97 reverses, a time required for the ultrasonic wave to travel a propagation distance L to and from the reflection section 33 in the measurement chamber 28 can be found. It is known that a speed C at which an ultrasonic wave propagates through a certain medium is in accordance with the following expression:

$$C = \sqrt{\frac{RT \sum C_{pn} X_n}{\sum C_{vn} X_n \sum M_n X n}} \quad (1)$$

This expression (1) is a general expression which is established for a gas in which plural components are mixed, and a variable n is a suffix indicating that the expression concerns an nth component. Therefore, $C_{pn}$ represents a constant pressure specific heat of the nth component of the gas existing in the measurement chamber 28, $C_{vn}$ represents an isovolumetric specific heat of the nth component of the gas in the measurement chamber 28, $M_n$ represents a molecular weight of the nth component, and $X_n$ represents a concentration ratio of the nth component. In addition, R represents a gas constant and T represents a temperature of the gas in the measurement chamber 28.

The propagation speed C is defined by the temperature T and the concentration ratio $X_n$ of the gas in the measurement chamber 28. The propagation speed C of an ultrasonic wave can be expressed as follows using the propagation distance L from the piezoelectric element 51 to the reflecting section 33:

$$C = 2 \times L/\Delta t \quad (2)$$

Therefore, if Δt is measured, the concentration ratio $X_n$, that is, a gasoline concentration can be found. It will be appreciated that, although a concentration of gasoline vapor was detected in this embodiment, in the case in which a concentration is already known, it is also possible to use the gas sensor as a sensor for finding the temperature T and the propagation distance L.

The microprocessor 91 performs an arithmetic operation in accordance with the above expression at a high speed and outputs a signal corresponding to the determined gasoline concentration via the D/A converter 92. This signal SGNL is outputted to the outside via the terminal 31b of the connector 31. In the embodiment, this signal SGNL is outputted to a computer, which controls a fuel injection amount of an internal combustion engine, and is used here for processing such as correcting the fuel injection amount taking into account a purge amount of gasoline from a canister.

(E) Actions and Effects of the First Embodiment

Figure 9:
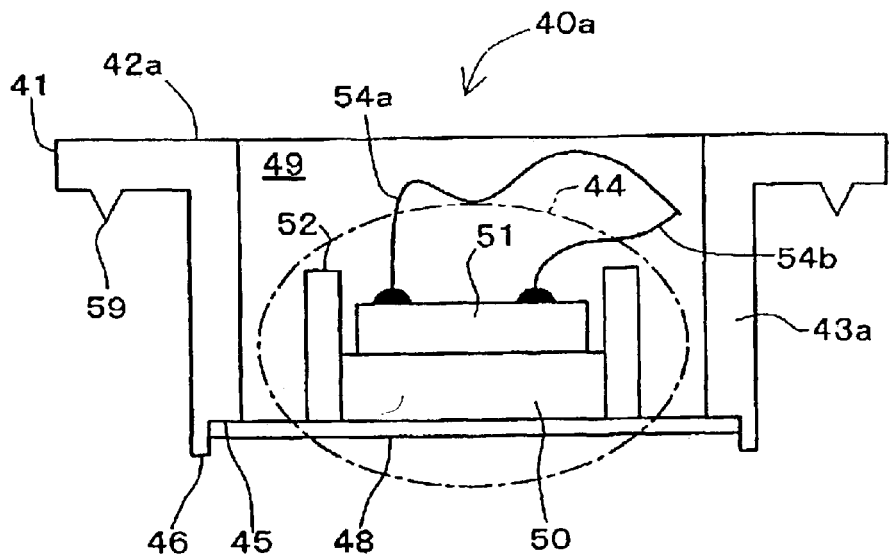
FIGS. 9(A–B) are schematic views showing a change in a state of the detection element main body 40 in the case of an element case 42 without a taper.
Figure 9:
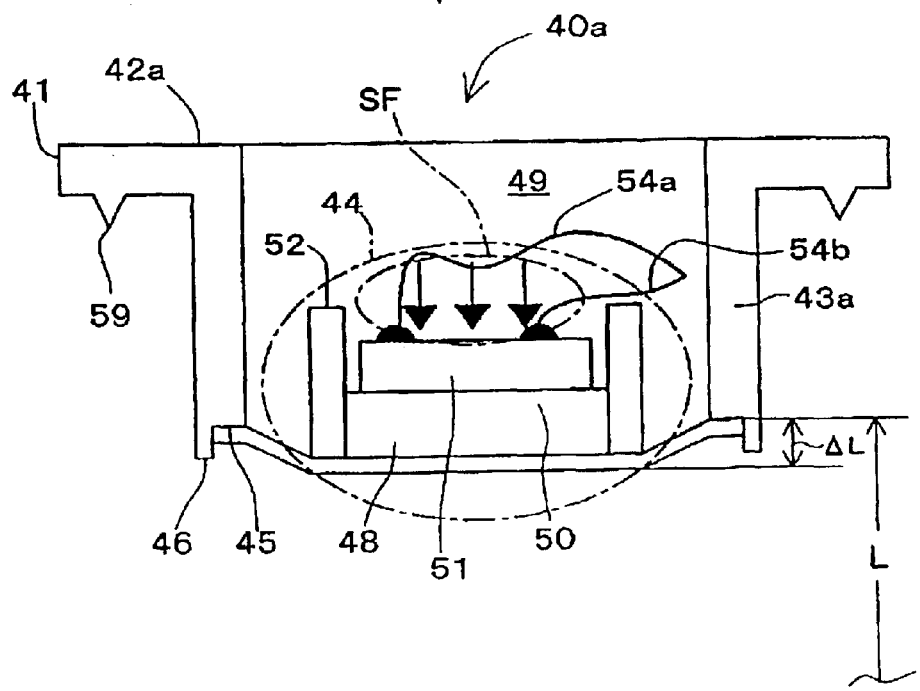
Figure 10:
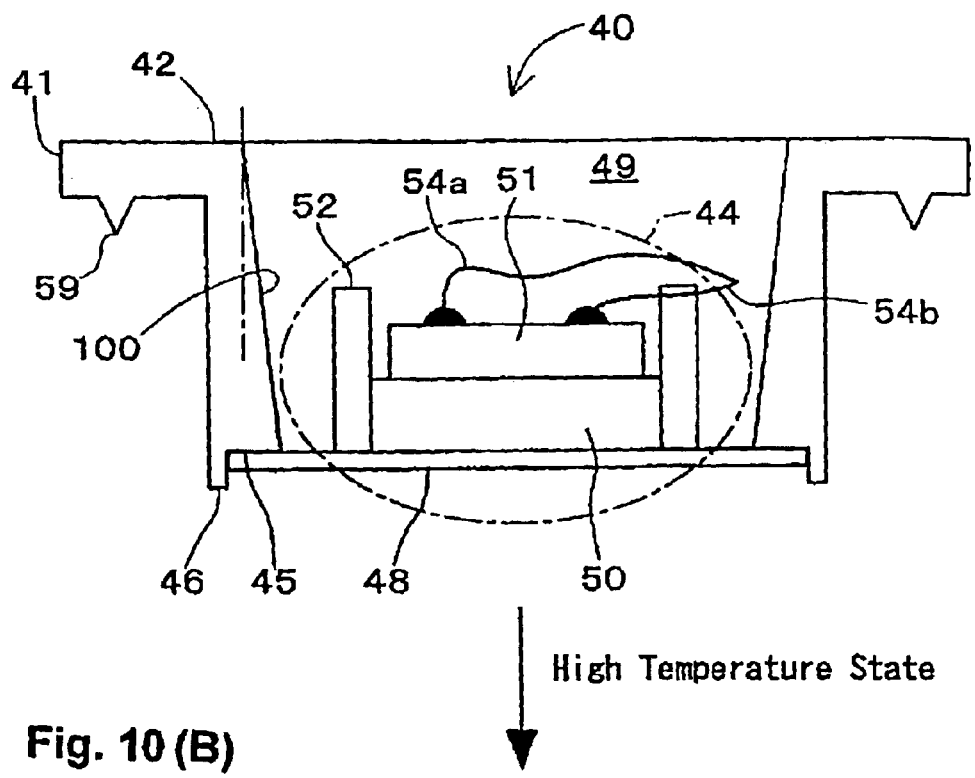
FIGS. 10(A–B) are schematic views showing a change in a state of the detection element main body 40 in the case of an element case 42 with a taper.
Figure 10:
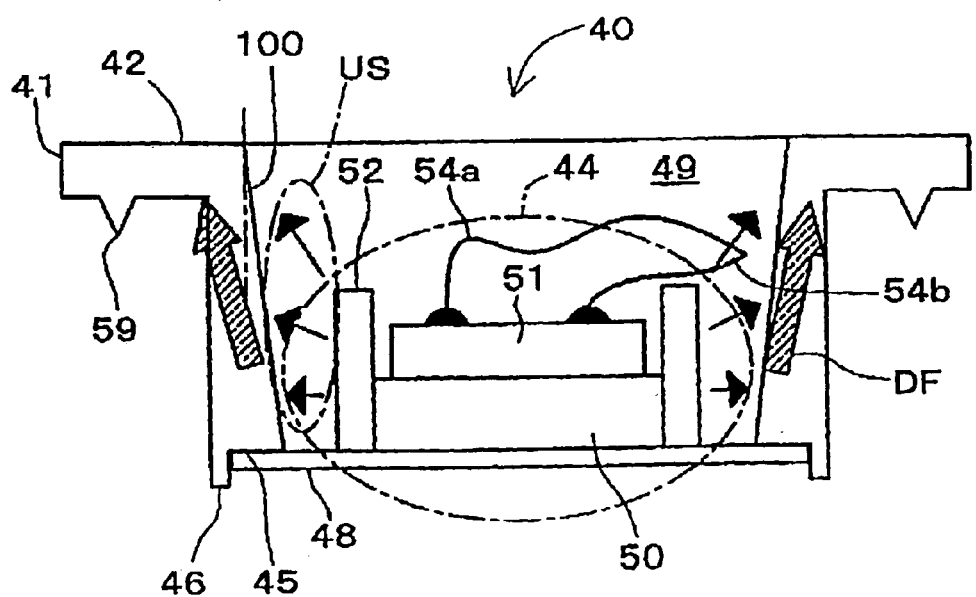
Figure 12:
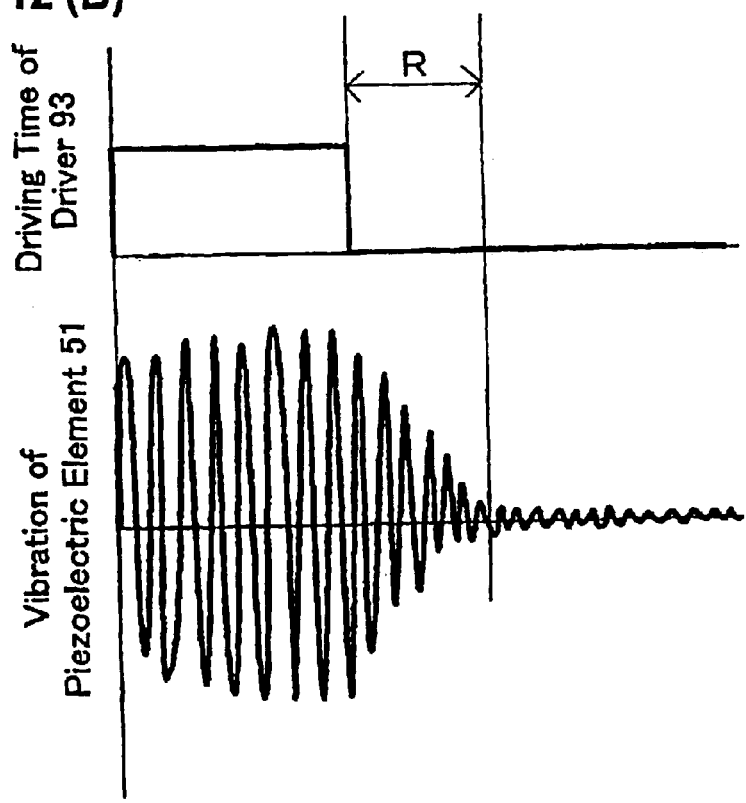
FIGS. 12(A–B) are a table and time chart of results of an experiment in which a reverberation was measured with respect to three types of taper angle.

In the first embodiment described above, a predetermined angle is provided on the internal peripheral surface of the element case 42 to form the internal peripheral surface 100 as the taper surface 100. By forming the element case 42 in such a shape, decrease in a detection accuracy of the gas sensor 10 and generation of noises are suppressed even at the time of high temperature. A reason for this will be described according to FIGS. 9 to 12. FIGS. 9 and 10 are explanatory views schematically showing a state of the detection element main body 40 in the case in which a filler has expanded. Note that, in these figures, only end faces are shown for several components and illustration of hatching indicating a cross section is omitted for convenience of understanding. In addition, the respective layers 52a, 52b, and 52c forming the tube body 52 are drawn integrally. Moreover, illustration of the terminals 55a and 55b as well as the projecting portions 56a and 56b is omitted for simplification.

In order to compare with the detection element main body 40 of this embodiment, a structure of a detection element main body 40a in which an internal periphery of the element case 42a is formed vertically is shown in FIG. 9. As shown in the figure, in the detection element main body 40a using an element case 42a in which an internal peripheral surface is vertical and is not formed as a taper surface, when its temperature rises and the filler 49 thermally expands, the filler 49 mainly pushes itself out in a vertical direction to increase its volume. In the detection element main body 40a shown in FIG. 9(A), since the internal peripheral surface of the element case 42a is vertical and a housing section 43a is a ring-shaped, when the filler 49 expands, a change in volume in a diameter direction rarely occurs. Consequently, as shown in FIG. 9(B), inside the detection element main body 40a, the element portion 44 is subjected to a strong force (internal stress) SF in a direction of the protective film 48, and the element portion 44 projects to the measurement chamber 28 side while involving deformation of the protective film 48. As a result, a distance between the upper surface of the piezoelectric element 51 and the terminals 55a and 55b is increased, and it becomes likely that disconnection of the lead wires 54a and 54b is caused. In addition, since the element portion 44 projects to the measurement chamber 28 side while involving deformation of the protective film 48, the propagation distance L to the reflecting section 33 is also reduced by a projection amount ΔL. As a result, an error occurs in the already described expression (2) for finding the propagation speed C of an ultrasonic wave for measuring a gas concentration in the measurement chamber 28, a detection accuracy of a gas concentration also decreases. In addition, since a change in volume in the diameter direction is regulated inside the element case 42*a*, a strong stress is generated in the diameter direction, which affects the piezoelectric element 51. Thus, a phenomenon in which vibration of the piezoelectric element 51 does not attenuate over a long time after driving is finished by the driver 93, a so-called reverberation also tends to occur. If this reverberation lasts for a long time, since it may become a large noise in detection of an ultrasonic wave reflected on the reflecting section 33, a detection accuracy of the element for detection main body 40*a* further decreases.

On the other hand, in this embodiment, as shown in FIG. 10(A), the internal peripheral surface of the element case 42 is formed as the taper surface 100 which inclines at a predetermined angle with respect to the vertical direction. Consequently, as shown in FIG. 10(B), when the filler 49 thermally expands, on the taper surface 100 of the internal periphery of the element case 42, the filler 49 is subjected a component of force DF in the upward direction (direction to the flange section 41) by the taper surface 100, and the expanded filler 49 causes a change in volume mainly in the upward direction. As a result, deformation of the protective film 48 is also reduced, and the element portion 44 including the piezoelectric element 51 naturally never projects to the measurement chamber 28 side. Therefore, the likelihood of disconnection of the lead wires 54*a* and 54*b* is eliminated. Moreover, since the protective film 48 does not deform, the propagation distance L to the reflecting section 33 does not change largely due to a rise in temperature either. Consequently, durability of the protective film 48 also increases. In addition, the internal stress SF in the diameter direction generated by the expansion of the filler 49 is eased, and occurrence of a reverberation is also suppressed.

An effect realized by forming the taper surface 100 described in this embodiment will be indicated as specific numerical values. FIG. 11 is an explanatory table showing a result of an experiment for measuring the projection amount ΔL shown in FIG. 9(B). As shown in FIG. 11, in the experiment, plural detection element main bodies of the following three types were formed:

(1) the detection element main body 40*a* in which the internal peripheral surface of the element case 42*a* is formed vertically (angle zero);

(2) the detection element main body 40 in which the internal peripheral surface of the element case 42 is formed as the taper surface 100 inclined at 11 degrees with respect to the vertical direction; and (3) a not-shown detection element main body in which an internal peripheral surface of an element case is formed as the taper surface 100 inclined at 15 degrees with respect to the vertical direction. A heat cycle of −40° C. to 125° C. was applied to each of three detection element main bodies six times, and thereafter the projection amount ΔL was measured. In FIG. 11, an average value of measurement values of the plural samples is shown. The projection amount ΔL is a value found by measuring how much the front end of the protective film 48 projected compared with a state before applying the heat cycle to it. From the experiment, it is seen that, by setting an angle of the taper on the internal peripheral surface of the element case 42 to a range of approximately 11 degrees ±4 degrees, the projection amount ΔL of the element portion 43 is reduced to approximately zero, and the projection of the protective film 48 due to thermal expansion of the filler 49 is suppressed significantly.

In addition, by forming the internal peripheral surface of the element case 42 as the taper surface 100 inclined at a predetermined angle, an ultrasonic vibration reflecting on the element case 42 to return, that is, a reverberation can also be reduced. In an experiment, plural detection element main bodies of the following three types were formed:

(1) the detection element main body 40*a* in which the internal peripheral surface of the element case 42*a* is formed vertically (angle zero);

(2) the detection element main body 40 in which the internal peripheral surface of the element case 42 is formed as the taper surface 100 inclined at 11 degrees with respect to the vertical direction; and (3) a not-shown detection element main body in which an internal peripheral surface of an element case is formed as the taper surface 100 inclined at 15 degrees with respect to the vertical direction. A reverberation in the case in which their environmental temperature was increased to 85° C. was measured. A result of the experiment is shown in FIG. 12(A). Turning briefly to FIG. 12(B), a measured reverberation time means a time R since the driving of the piezoelectric element 51 by the driver 93 ends until the vibration of the piezoelectric element 51 itself attenuates to a predetermined value or less.

As shown in FIG. 12(A), among the three types of detection element main bodies, the reverberation time R became shortest when the internal peripheral surface of the element case 42 was formed as the taper surface 100 inclined 11 degrees with respect to the vertical direction. There are several possible reasons for this. For one thing, it is possible that the stress SF due to the thermal expansion of the filler 49 is released upward by the taper surface 100 and a large stress is not applied to the piezoelectric element 51. In an element in which a distance between gratings is changed by an electric energy and mechanical displacement results as in the piezoelectric element, when a force is applied to the element itself and distortion remains inside, even after an electric signal from the outside is removed, various forces remain inside the element, which is likely to prevent attenuation of vibration. In addition, an ultrasonic wave propagating in a direction other than to the measurement chamber 28 side from the piezoelectric element 51 exists to some extent and a reverberation also increases by the ultrasonic wave reflecting on the element case 42 or the like to return. However, when the internal peripheral surface of the element case 42 is formed as the taper surface 100 inclined at 11 degrees, it is possible that an influence of the reflection of the ultrasonic wave decreases.

As described above, in the detection element main body 40 of this embodiment, projection of the element portion 44 to the measurement chamber 28 side involving deformation of the protective film 48 is suppressed, and a reverberation after vibration of the piezoelectric element 51 is also reduced. As a result, even under conditions in which the filler 49 expands (e.g., at high temperature time), decrease of a measurement accuracy of the gas sensor 10 can be suppressed. Therefore, if this is used for concentration detection of vapor of a fuel (gasoline, fuel oil, etc.) of an internal combustion engine, a concentration of a fuel gas can be detected with a high accuracy even in the vicinity of the internal combustion engine where a change in temperature is large. A gas concentration detecting device constituted by using this gas sensor 10 may be used for detection of a concentration of gasoline or the like purged from a canister or the like. It is also possible to apply it to detection of a gas concentration in an air-fuel mixture taken into a cylinder from an inlet pipe.

Figure 13:
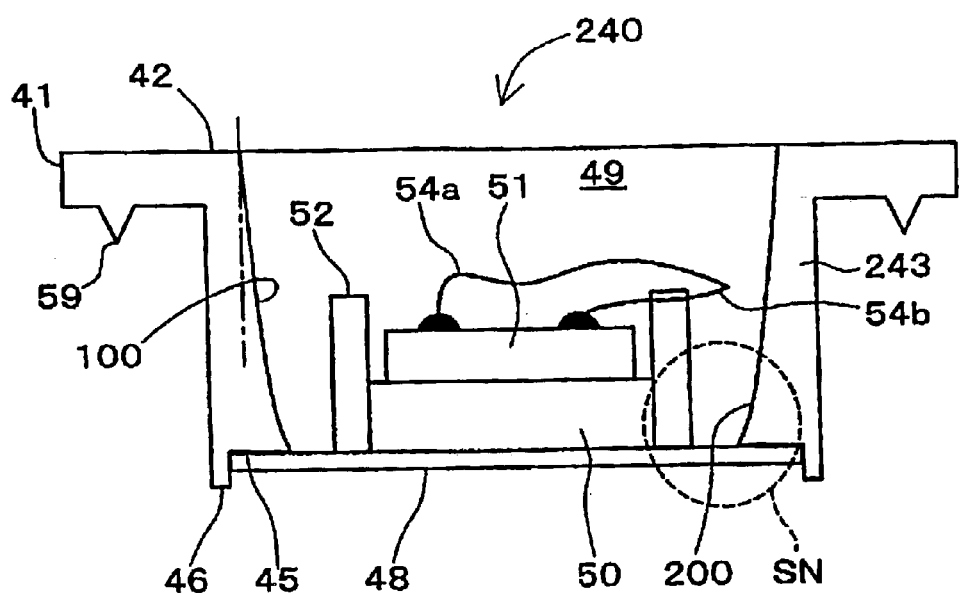
FIG. 13 is a schematic view of a detection element main body 240 according to a second embodiment.

(F) Second Embodiment:

Next, a second embodiment of the present invention will be described. As shown in FIG. 13, a gas sensor of the second embodiment has a housing section 243 which is different from the housing section 43 of the first embodiment only in a shape of an internal peripheral surface 200 thereof, and other components of the housing section 243 are identical with those of the housing section 43. As shown in the figure, the internal peripheral surface 200 of the housing section 243 is curved in a sectional shape in an axial direction thereof to swell out to an inner side of the housing section 243 on a side closer to the protection film 48. In this embodiment, an internal peripheral side of a section of the housing section 243 is formed as a taper surface inclined at 11 degrees in its upper part and formed in an arc as a tangential surface with the taper surface in its lower part which is approximately one third of the internal peripheral surface (part denoted by reference symbol SN in the figure).

Figure 14:
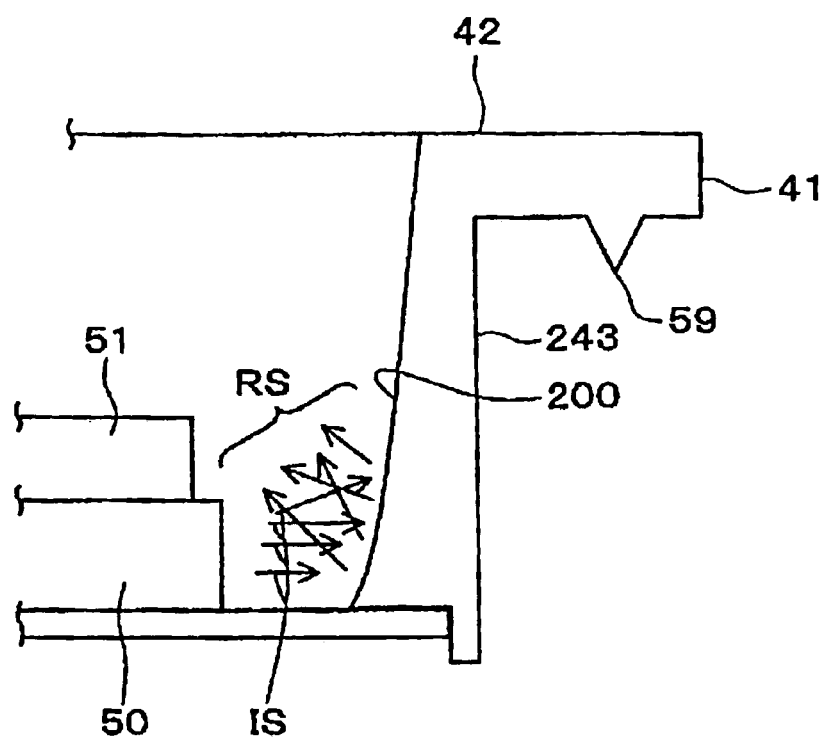
FIG. 14 is a partial schematic view of an internal peripheral surface 200 of a housing section 243 of the second embodiment.

The internal peripheral surface 200 of the housing section 243 is shown in FIG. 14 in an enlarged form. As shown in the figure, since the internal peripheral surface 200 of the housing section 243 is formed in an arc shape in a section in its lower part, when an ultrasonic wave vibration (reference symbol IS in the figure) propagating from the piezoelectric element 51 or the acoustic matching plate 50 in a lateral direction thereof reflects on the internal peripheral surface 200, the vibration spreads in various directions. That is, reflected waves (reference symbol RS in the figure) rarely propagate in a specific direction. As a result, reverberation due to the reflection or the like on the internal peripheral surface of the housing section 243 is reduced more efficiently.

Figure 15:
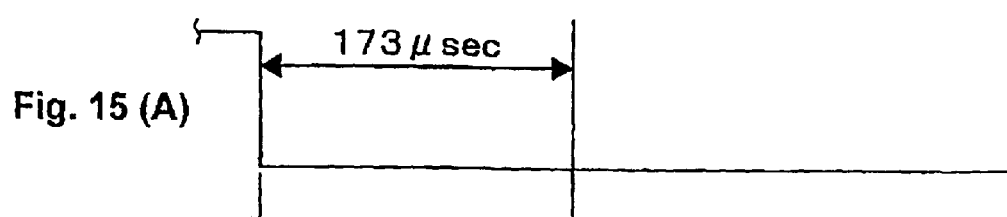
FIGS. 15(A–C) are timing charts of reverberation time.
Figure 15:
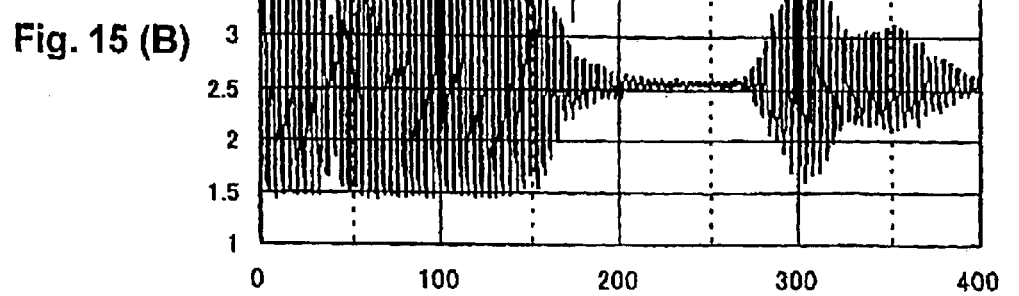
Figure 15:
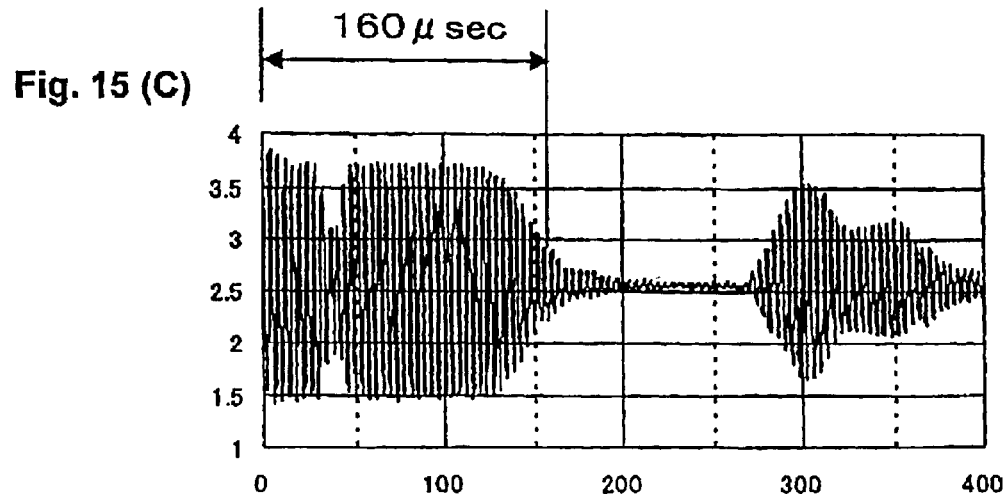

An observational example of the reverberation in the second embodiment is shown in FIG. 15. As shown in FIGS. 15(A and B), the detection element main body 40 of the gas sensor 10 of the first embodiment required 173 μsec since a signal for excitation from the outside was removed until a vibration of the element fell below a predetermined value due to an influence of the reverberation. As shown in FIG. 15(C), in the detection element main body 240 of the second embodiment tested under the identical conditions, the time until the vibration of the element fell below the predetermined value was 160 μsec (C). Results obtained by testing with several samples were substantially identical, which indicates that reverberation time was reduced by approximately 10 to 20 μsec.

Although only the lower part SN of the internal peripheral surface 200 of the housing section 243 is made a part of an arc in the second embodiment, the entire internal peripheral surface 200 may be formed in a gentle arc shape. In addition, it is allowable that, in place of a part of the arc, the sectional shape of the lower part SN is changed to a part of an ellipse, a part of a parabola, a part of a hyperbola, a free curve, or the like. In the case in which the sectional shape of the lower part SN is changed to a part of an ellipse or a parabola, it is also preferable to make an arrangement such that the piezoelectric element 51 or the acoustic matching plate 50 is not located in the focal point of the curve.

Although a few non-limiting illustrative embodiments of the present invention have been described, it will be appreciated that the present invention is not limited to such embodiments but can be carried out in various and numerous other embodiments without departing from the scope of the invention. For example, a structure may be provided in which an ultrasonic element for transmission and that for reception are separated, and a structure may be provided in which the external peripheral wall of the element case 42 is tapered in the same manner as the internal peripheral surface 100.

What is claimed is:

1. A gas sensor for detecting at least one characteristic of a gas existing in a predetermined flow path, comprising:

a vibration element for detecting characteristics of the gas utilizing a change in a dilatational wave propagating through the gas; and a tubular element case housing the vibration element, wherein an internal peripheral surface of the element case has a smaller inner diameter in a part closer to one end side where the vibration element is arranged, the vibration element is embedded in a filler filled in the element case, and at least a part of the internal peripheral surface of the element case adjoining a side edge of the vibration element is a taper surface having an inner diameter narrowed toward the one end side.

2. A gas concentration detecting device, which is mounted on equipment with an engine that burns a volatile fuel, and which detects a concentration of the volatile fuel, comprising:

a flow path provided in a part of a fuel passage to the engine;

a gas sensor according to claim 1, which is provided facing the flow path; and an arithmetic circuit which is connected to the vibration element of the gas sensor and detects a speed at which a dilatational wave caused by vibration of the vibration element passes the flow path, thereby calculating a concentration of the fuel in the flow path.

3. A gas sensor according to claim 1, wherein the dilatational wave is one of an acoustic wave and an ultrasonic wave, and the vibration element is for one of generating and receiving the dilatational wave.

4. A gas sensor according to claim 1, wherein an angle defined between the taper surface and an axial direction of the element case is in a range between 7 to 15 degrees.

5. A gas sensor according to claim 4, wherein the angle is in a range between 10 to 12 degrees.

6. A gas sensor according to claim 1, wherein the element case comprises a housing section and a flange section which is jointly provided at the other end side which is opposite the one end side of the housing section and attaches the element case to the flow path.

7. A gas sensor according to claim 6, wherein the element case is formed in a shape in which an external peripheral surface and the internal peripheral surface of the housing section are not parallel to each other, and a thickness of the housing section gradually increases from a joint portion of the housing section and the flange section toward the housing section.

8. A gas sensor for detecting at least one characteristic of a gas existing in a predetermined flow path, comprising:

a vibration element for detecting characteristics of the gas utilizing a change in a dilatational wave propagating through the gas; and a tubular element case housing the vibration element, wherein an internal peripheral surface of the element case has a smaller inner diameter in a part closer to one end side where the vibration element is arranged, the vibration element is embedded in a filler filled in the element case, an at least a part of the internal peripheral surface of the element case is a curved surface having a smaller inner diameter in a part closer to the one end side.

9. A gas concentration detecting device, which is mounted on equipment with an engine that burns a volatile fuel, and which detects a concentration of the volatile fuel, comprising:

a flow path provided in a part of a fuel passage to the engine;

a gas sensor according to claim 8, which is provided facing the flow path; and an arithmetic circuit which is connected to the vibration element of the as sensor and detects a speed at which a dilatational wave caused by vibration of the vibration element passes the flow path, thereby calculating a concentration of the fuel in the flow path.

10. A gas sensor according to claim 8, wherein the curved surface is a part of one of a circle, an ellipse, a parabola, and a hyperbola in a section in an axial direction of the element case.

11. A gas sensor according to claim 8, wherein the dilatational wave is one of an acoustic wave and an ultrasonic wave, and the vibration element is for one of generating and receiving the dilatational wave.

12. A gas sensor according to claim 8, wherein the element case comprises a housing section and a flange section which is jointly provided at the other end side which is opposite the one end side of the housing section and attaches the element case to the flow path.

13. A gas sensor according to claim 12, wherein the element case is formed in a shape in which an external peripheral surface and the internal peripheral surface of the housing section are not parallel to each other, and a thickness of the housing section gradually increases from a joint portion of the housing section and the flange section toward the housing section.

\* \* \* \* \*